(12) United States Patent
Borillo et al.

(10) Patent No.: US 7,399,308 B2
(45) Date of Patent: Jul. 15, 2008

(54) VASCULAR FILTER SYSTEM

(75) Inventors: Thomas Borillo, Plymouth, MN (US); Mark Maciejewski, Edna, MN (US); Gregg S. Sutton, Maple Grove, MN (US); Jeffrey Welch, New Hope, MN (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 10/198,670

(22) Filed: Jul. 19, 2002

(65) Prior Publication Data

US 2003/0060844 A1     Mar. 27, 2003

Related U.S. Application Data

(63) Continuation of application No. 10/045,296, filed on Nov. 7, 2001, now abandoned, which is a continuation-in-part of application No. 09/249,377, filed on Feb. 12, 1999, now Pat. No. 6,391,044.

(51) Int. Cl.
*A61F 2/01* (2006.01)
(52) U.S. Cl. ..................................... 606/200
(58) Field of Classification Search ................. 606/200, 606/1, 159, 198
See application file for complete search history.

(56) References Cited

U.S. PATENT DOCUMENTS

| | | |
|---|---|---|
| 3,435,824 A | 4/1969 | Gamponia |
| 3,889,685 A | 6/1975 | Miller, Jr. et al. |
| 3,952,747 A | 4/1976 | Kimmell, Jr. |
| 4,230,119 A | 10/1980 | Blum |
| 4,349,029 A | 9/1982 | Mott |
| 4,425,908 A | 1/1984 | Simon |
| 4,494,531 A | 1/1985 | Gianturco |
| 4,545,390 A | 10/1985 | Leary |
| 4,619,246 A | 10/1986 | Molgaard-Nielsen et al. |
| 4,619,274 A | 10/1986 | Morrison |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |

(Continued)

FOREIGN PATENT DOCUMENTS

CA         2250777        2/1998

(Continued)

OTHER PUBLICATIONS

A. Cragg et al., A New Percutaneous Vena Cava Filter, AJR, 141, Sep. 1983, pp. 601-604.

(Continued)

*Primary Examiner*—Todd e. Manahan
*Assistant Examiner*—Michael G Mendoza (57) ABSTRACT

A removable vascular filter system for capture and retrieval of emboli while allowing continuous perfusion of blood, comprising a porous filter membrane and a filter membrane support structure. This system is useful for any percutaneous angioplasty, stenting, thrombolysis or tissue ablation procedure. The system may minimize the incidence of stroke, myocardial infarction or other clinical complications that may be associated with these procedures.

1 Claim, 11 Drawing Sheets

U.S. PATENT DOCUMENTS

| | | |
|---|---|---|
| 4,793,348 A | 12/1988 | Palmaz |
| 4,794,928 A | 1/1989 | Kletschka |
| 4,832,055 A | 5/1989 | Palestrant |
| 4,842,579 A | 6/1989 | Shiber |
| 4,873,978 A | 10/1989 | Ginsburg |
| 4,884,573 A | 12/1989 | Wijay et al. |
| 4,921,484 A | 5/1990 | Hillstead |
| 4,926,858 A | 5/1990 | Gifford, III et al. |
| 4,957,501 A | 9/1990 | Lahille et al. |
| 4,969,891 A | 11/1990 | Gewertz |
| 4,990,156 A | 2/1991 | Lefebvre |
| 5,011,488 A | 4/1991 | Ginsburg |
| 5,053,008 A | 10/1991 | Bajaj |
| 5,059,205 A | 10/1991 | El-Nounou et al. |
| 5,092,839 A | 3/1992 | Kipperman |
| 5,095,915 A | 3/1992 | Engelson |
| 5,100,423 A | 3/1992 | Fearnot |
| 5,108,419 A | 4/1992 | Reger et al. |
| 5,133,733 A | 7/1992 | Rasmussen et al. |
| 5,152,777 A | 10/1992 | Goldberg et al. |
| 5,190,540 A | 3/1993 | Lee |
| 5,190,546 A | 3/1993 | Jervis |
| 5,201,757 A | 4/1993 | Heyn et al. |
| 5,242,462 A | 9/1993 | El-Nounou et al. |
| 5,246,445 A | 9/1993 | Yachia et al. |
| 5,279,546 A | 1/1994 | Mische et al. |
| 5,324,304 A | 6/1994 | Rasmussen |
| 5,329,942 A | 7/1994 | Gunther et al. |
| 5,372,600 A | 12/1994 | Beyar et al. |
| 5,413,586 A | 5/1995 | Dibie et al. |
| 5,421,832 A | 6/1995 | Lefebvre |
| 5,423,849 A | 6/1995 | Engelson et al. |
| 5,496,277 A | 3/1996 | Termin et al. |
| 5,531,788 A | 7/1996 | Dibie et al. |
| 5,549,626 A | 8/1996 | Miller et al. |
| 5,613,949 A | 3/1997 | Miraki |
| 5,632,660 A | 5/1997 | Sheiban et al. |
| 5,662,631 A | 9/1997 | Marx |
| 5,662,671 A | 9/1997 | Barbut et al. |
| 5,681,347 A | 10/1997 | Cathcart et al. |
| 5,695,519 A | 12/1997 | Summers et al. |
| 5,709,704 A | 1/1998 | Nott et al. |
| 5,749,890 A | 5/1998 | Shaknovich |
| 5,769,816 A * | 6/1998 | Barbut et al. ................... 604/96 |
| 5,779,716 A | 7/1998 | Cano et al. |
| 5,807,398 A | 9/1998 | Shaknovich |
| 5,810,874 A | 9/1998 | Lefebvre |
| 5,814,064 A | 9/1998 | Daniel et al. |
| 5,827,324 A | 10/1998 | Cassell et al. |
| 5,836,969 A | 11/1998 | Kim et al. |
| 5,848,964 A | 12/1998 | Samuels |
| 5,876,367 A | 3/1999 | Kaganov et al. |
| 5,902,263 A | 5/1999 | Patterson et al. |
| 5,910,154 A | 6/1999 | Tsugita et al. |
| 6,001,118 A | 12/1999 | Daniel et al. |
| 6,013,093 A | 1/2000 | Nott et al. |
| 6,051,014 A * | 4/2000 | Jang ........................... 606/200 |
| 6,053,932 A | 4/2000 | Daniel et al. |
| 6,059,814 A | 5/2000 | Ladd |
| 6,059,825 A | 5/2000 | Hobbs et al. |
| 6,068,621 A | 5/2000 | Balceta et al. |
| 6,074,357 A | 6/2000 | Kaganov et al. |
| 6,080,178 A | 6/2000 | Meglin |
| 6,126,673 A | 10/2000 | Kim et al. |
| 6,152,946 A | 11/2000 | Broome et al. |
| 6,165,179 A | 12/2000 | Cathcart et al. |
| 6,165,200 A | 12/2000 | Tsugita et al. |
| 6,168,604 B1 | 1/2001 | Cano |
| 6,179,859 B1 | 1/2001 | Bates et al. |
| 6,179,861 B1 | 1/2001 | Khosravi et al. |
| 6,187,015 B1 | 2/2001 | Brenneman |
| 6,203,561 B1 | 3/2001 | Ramee et al. |
| 6,214,025 B1 | 4/2001 | Thistle et al. |
| 6,221,096 B1 | 4/2001 | Aiba et al. |
| 6,235,044 B1 * | 5/2001 | Root et al. ................... 606/200 |
| 6,241,746 B1 | 6/2001 | Bosma et al. |
| 6,258,115 B1 | 7/2001 | Dubrul |
| 6,267,776 B1 | 7/2001 | O'Connell |
| 6,267,777 B1 | 7/2001 | Bosma et al. |
| 6,270,513 B1 | 8/2001 | Tsugita et al. |
| 6,273,900 B1 | 8/2001 | Nott et al. |
| 6,277,138 B1 | 8/2001 | Levinson et al. |
| 6,280,432 B1 | 8/2001 | Turovskiy et al. |
| 6,290,710 B1 | 9/2001 | Cryer et al. |
| 6,336,934 B1 | 1/2002 | Gilson et al. |
| 6,346,116 B1 | 2/2002 | Brooks et al. |
| 6,726,701 B2 | 4/2004 | Gilson et al. |
| 2004/0006368 A1 * | 1/2004 | Mazzocchi et al. .......... 606/200 |

FOREIGN PATENT DOCUMENTS

| | | |
|---|---|---|
| CA | 2310756 | 7/1999 |
| EP | 0737450 | 4/1996 |
| EP | 0791340 | 2/1997 |
| EP | 1179321 | 8/2001 |
| FR | 2606642 | 11/1986 |
| FR | 2652267 | 3/1991 |
| GB | 2020557 A | 11/1979 |
| JP | 5-137729 | 6/1993 |
| JP | 7088192 | 4/1995 |
| SU | 764684 | 1/1978 |
| SU | 764684 * | 9/1980 |
| WO | 96/01591 * | 1/1996 |
| WO | 96/01591 A1 | 1/1996 |
| WO | 97/17100 A1 | 5/1997 |
| WO | 98/33444 A1 | 8/1998 |
| WO | 98/39053 A1 | 9/1998 |
| WO | 99/23976 A1 | 5/1999 |
| WO | 99/58068 A2 | 11/1999 |
| WO | 00/16705 A1 | 3/2000 |
| WO | 01/58382 A2 | 8/2001 |
| WO | 02/056955 A1 | 7/2002 |
| WO | 02/071920 A2 | 9/2002 |

OTHER PUBLICATIONS

A. Cragg et al., Nonsurgical Placement of Arterial Endoprosthesis; A New Technique Using Nitinol Wire, AJR, Apt. 1983, pp. 261-263.

G. Lund et al., Long-Term Patency of the Ductus Arteriosus After Balloon Dilation: An Expermental Study, AJR, Sep. 1983, p. 772.

M. H. Wholey et al., PTA and Stents in the Treatment of Extraclavical Circulation, Journal of Advanced Cardiology vol. 9 Suppl. E. 1996, pp. 25E-30E.

Topol, Eric J., et al., Recognition of the Importance of Embolization in Artherosclerotic Vascular Disease Circulation, pp. 570-580, 2000.

Eichelter, et al., Prophylaxis of Pulmonary Embolism, Archives of Surgery, vol. 97, Aug. 1968, pp. 348-356.

Greenfield, et al., A New Intercaval Filter Permitting Continued Flow and Resolution of Emboli, Surgery, vol. 73, No. 4, pp. 599-606.

* cited by examiner

VASCULAR FILTER SYSTEM

CROSS-REFERENCE TO RELATED APPLICATIONS

This patent application is a continuation of, U.S. patent application Ser. No. 10/045,296, filed Nov. 7, 2001, now abandoned, which is a continuation-in-part of U.S. patent application Ser. No. 09/249,377, filed Feb. 12, 1999, now U.S. Pat. No. 6,391,044.

BACKGROUND OF THE INVENTION

I. Field of the Invention

The present invention relates to the treatment of vascular disease by either percutaneous angioplasty and stenting or surgery. More particularly, the present invention relates to a system that reduces macro- and micro-embolization during the treatment of vascular disease.

II. Discussion of the Related Art

A variety of surgical and non-surgical angioplasty procedures have been developed for removing obstructions from blood vessels. Balloon angioplasty utilizes a balloon-tipped catheter which may be inserted within a stenosed region of the blood vessel. By inflation of the balloon, the stenosed region is dilated. Stenting involves the permanent implantation of a metallic scaffold in the area of the obstruction, following balloon dilatation. The stent is often delivered on an angioplasty balloon, and is deployed when the balloon is inflated. Another alternative is the local delivery of medication via an infusion catheter. Other techniques, such as atherectomy, have also been proposed. In atherectomy, a rotating blade is used to shave plaque from an arterial wall. Finally, other techniques, such as tissue ablation, are sometimes performed to address electrical anomalies in heart rhythm. Surgery involves either removing the plaque from the artery or attaching a graft to the artery so as to bypass the obstructing plaque.

One problem common to all of these techniques is the accidental release of portions of the plaque or thrombus, resulting in emboli which can lodge elsewhere in the vascular system. Such emboli may be dangerous to the patient, and may cause severe impairment of the distal circulatory bed. Depending upon the vessel being treated, this may result in a stroke or myocardial infarction or limb ischemia.

Vascular filters or embolism traps for implantation into the vena cava of a patient are well known, being illustrated by, for example, U.S. Pat. Nos. 4,727,873 and 4,688,533. Additionally, there is a substantial amount of medical literature describing various designs of vascular filters and reporting the results of the clinical and experimented use thereof. See, for example, the article by Eichelter & Schenk entitled "Prophylaxis of Pulmonary Embolism," Archives of Surgery, Vol. 97, August 1968, pp. 348 et seq. See, also, the article by Greenfiled, et al., entitled "A New Intracaval Filter Permitting Continued Flow and Resolution of Emboli", Surgery, Vol. 73, No. 4, pp. 599-606 (1973).

Vascular filters are used, often during a postoperative period, when there is a perceived risk of a patient encountering a pulmonary embolus resulting from clots generated at the surgical site. Typically, the filter is mounted in the vena cava to catch large emboli passing from the surgical site to the lungs.

The vascular filters of the prior art are usually permanently implanted in the venous system of the patient, so that even after the need for the filter has abated, the filter remains in place for the lifetime of the patient, absent surgical removal. U.S. Pat. No. 3,952,747 describes a stainless steel filtering device which is permanently implanted transvenously within the inferior vena cava. The filtering device is intended to treat recurrent pulmonary embolism. U.S. Pat. No. 4,873,978 describes a catheter device comprising a catheter body having a strainer mounted at its distal end. The strainer is shiftable between an opened configuration where it extends substantially across the blood vessel to entrap passing emboli, and a closed configuration where it retains the captured emboli during removal of the catheter. A mechanism actuable at the proximate end of the catheter body allows selective opening and closing of the strainer. Typically, the strainer is a collapsible cone having an apex attached to a wire running from the distal end to the proximate end of the catheter body.

Permanent implantation may be deemed medially undesirable, but it has been done because vascular filters are implanted in patients primarily in response to potentially life threatening situations. Accordingly, the potential disadvantages of permanent implantations of a vascular filter are often accepted.

Notwithstanding the usefulness of the above-described methods, a need still exists for an apparatus and method for preventing embolization associated with conventional surgery and interventional procedures. In particular, it would be desirable to provide a device which could be located within the vascular system to collect and retrieve portions of plaque and thrombus which have dislodged during the surgery or angioplasty procedure.

SUMMARY OF THE INVENTION

The present invention provides a vascular filter system useful in the surgical or interventional treatment of vascular disease. Macro- and micro-embolization may occur during percutaneous procedures such as angioplasty, which potentially increases the risk of a minor or major stroke. The system of the present invention for reducing macro- and micro-embolization is very useful in helping to prevent the risk of stroke. However, this system would also be useful in any percutaneous angioplasty, stenting, thrombolysis or tissue ablation procedure, or surgical procedure where embolization is a risk. The vascular filter system of the present invention may decrease embolism while allowing brain, or other distal tissue, perfusion. The filters may be incorporated into a guidewire which is used for the entire procedure from crossing a lesion to deploying a stent.

An objective of the present invention is to provide a vascular filter system for reducing macro- and micro-embolization. Another objective of the present invention is to provide a vascular filter system which is readily removable from the vascular system, or elsewhere, of a patient when the filter is no longer needed. It is a further objective of the present invention to provide a vascular filter system having a configuration which does not require hooks to penetrate and grip the blood vessel walls, so that the implantation results in less blood vessel injury. It is yet a further objective of the present invention to provide a vascular filter system of very low profile which is part of a guidewire and may be used in small vessels. It is yet a further objective of the invention to provide a vascular filter system for angioplasty, stenting, thrombolysis and/or electrophysiologic or other ablative procedures.

In one exemplary embodiment the filter comprises a thin membrane attached to the guidewire and supported by fine metal spines. Attachment of the filter membrane to the guidewire allows expansion of the filter membrane with a firm fit inside the artery. The attachment also allows for collapse of the filter membrane at the end of the procedure so it fits tightly against the guidewire and can be withdrawn through the guide catheter. In another exemplary embodiment, the filter membrane rests upon or is attached to a basket-like structure, at least one end of which is attached to the guidewire. The filter membrane has a pore size such that blood flow is not impeded when the filter membrane is expanded but micro- and macro-emboli are blocked. Expansion of the filter membrane is aided by the forward flow of blood against the filter. The filter design results in a very low profile so that the initial crossing of the lesion is minimally traumatic. Also, the small diameter and small profile facilitate use of the device in small or larger arteries with minimal or no obstruction of blood flow.

In another exemplary embodiment of the present invention, a dilatation balloon delivery system incorporating a vascular filter may be useful to capture thrombus or emboli generated during a cardiovascular procedure. The dilatation balloon delivery system comprises a balloon catheter having proximal and distal ends, the proximal end comprising a hub having ports. The distal end comprises an inflatable balloon having a distal end, where a guidewire lumen extends from the distal end of the balloon to one of the ports in the hub. The guidewire also extends distally to a vascular filter system. A sheath is arranged concentric to the balloon catheter, where the distal end of the sheath covers the inflatable balloon and the guidewire filter. The sheath proximal end extends to a point distal to the hub. The dilatation balloon delivery system may be an over-the-wire system, as described, or a rapid exchange system.

In another exemplary embodiment of the present invention, a stent delivery system incorporating a vascular filter may be useful to capture thrombus or emboli generated during a cardiovascular procedure. The stent delivery system comprises a balloon catheter having proximal and distal ends, the proximal end comprising a hub having ports. The distal end comprises an inflatable balloon having a distal end, where a guidewire lumen extends from the distal end of the balloon to one of the ports in the hub. The guidewire lumen also extends proximally to a vascular filter system. An expandable stent is positioned annularly around the balloon. A sheath is arranged concentric to the balloon catheter, where the distal end of the sheath covers the inflatable balloon, the stent, and the guidewire filter. The sheath proximal end extends to a point distal to the hub. The stent delivery system may be an over-the-wire system, as described, or a rapid exchange system.

In another exemplary embodiment of the present invention, the vascular filter is attached to a guidewire having an infusion catheter with infusion holes for controlled delivery and distribution of medication to the area of surgical intervention. The sheath over the guidewire may control the area of distribution of the medication by controlling the number of the revealed infusion holes in the infusion catheter. A locking mechanism on the proximal end of the apparatus may assure that the sheath does not reveal a larger than necessary area of the angioplasty, i.e., thrombus, to be exposed to the infusion holes.

In another exemplary embodiment of the present invention, a vascular filter system may be used to capture thrombus or emboli generated during electrophysiology or another ablative procedure. A guidewire-based collapsible filter basket can be advanced through the femoral artery to a position adjacent the left ventricle. The basket faces the ventricle, and then the basket is collapsed and withdrawn proximally. Alternately, a guiding catheter has a distally-extending filter membrane that may be collapsed, for example, by sliding an outer sheath distally.

An advantage of the present invention is that it provides the benefits of filtration and capture of embolic particulates, temporarily, during a variety of clinical procedures.

Given the following enabling description of the drawings, the apparatus should become evident to a person of ordinary skill in the art.

BRIEF DESCRIPTION OF THE DRAWINGS

The present invention will be apparent upon consideration of the following detailed description, taken in conjunction with the accompanying drawings, in which the reference characters refer to like parts throughout, and in which.

DETAILED DESCRIPTION OF THE PREFERRED EMBODIMENTS

The present invention relates to a vascular filter system for use in percutaneous angioplasty and stenting and provides for the prevention of distal embolism during endovascular procedures. Further, the filter system of the present invention allows for distal perfusion while preventing embolization.

The system comprises a thin, perforated filter membrane which is capable of blocking emboli and which is attached to the distal end of a guidewire. In one exemplary embodiment of the invention, a thin, flexible, perforated membrane is supported by four or more supports that form a distally extending basket. At least one end of the basket is attached to the guidewire, and the other, slidable end may be moved to cause the membrane to open or close.

Figure 1:
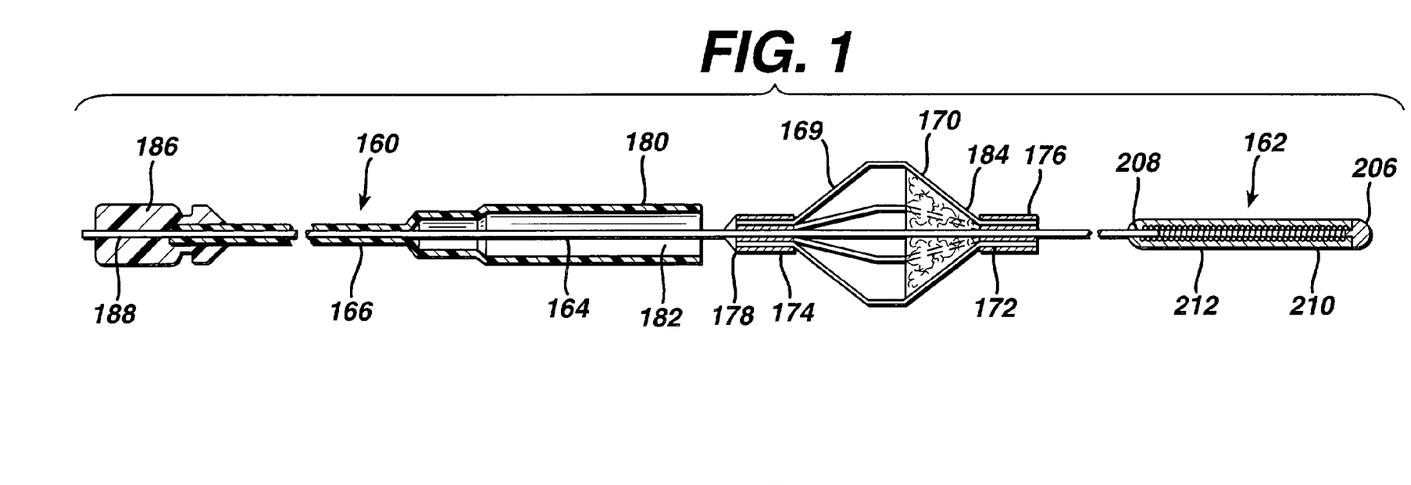
FIG. 1 illustrates a lateral, partial cross-sectional view of one exemplary embodiment of the present invention with the filter membrane in an open position.

The present invention can perhaps be better appreciated by reference to the drawings. FIG. 1 illustrates a lateral, cross-sectional view of a distal end of a guidewire 160 with a filter membrane 170 attached thereto. FIG. 1 illustrates guidewire 160 with a shapeable soft "floppy" tip 162 at its extreme distal end which provides flexibility and maneuverability to guidewire 160. The filter membrane in FIG. 1 is illustrated in an open position.

Guidewire 160 comprises a core wire 164, which extends into floppy tip 162, and a sheath 166. Filter membrane 170 is supported by a basket 169 comprising two or more filter basket wires 168, having distal ends 172 and proximal ends 174. Preferably, proximal marker 178 is fixedly attached to core wire 164, and distal marker 176, with a polymeric or metallic sleeve, is slidable over core wire 164.

The flow of blood in FIG. 1 is toward the distal end of guidewire 160. As such, the force of the flow of blood pushes on deployed filter membrane 170 and helps to maintain filter membrane 170 in the deployed position.

A sheath member 180 is attached to the distal end of sheath 166, sheath member 180 having a lumen 182 with a diameter and length sufficient to receive or slide over proximal marker 178. Sheath 166 and sheath member 180 may be either separate pieces bonded together or a continuous, integral structure. Sheath 166 and sheath member 180 are each made from low friction polymeric material, preferably polytetrafluoroethylene, polyethylene, nylon, or polyurethane.

Filter membrane 170 may comprise a number of different non-metallic permeable membranes having sufficient porosity to facilitate blood flow but having sufficiently small openings to capture emboli. Filter membrane 170 is preferably affixed at least at its distal portion 184 to core wire 164 and/or basket wire distal ends 172 and, optionally, to basket wires 168. The remainder of filter membrane 170 may be unattached or, preferably, attached to basket wires 168, such as by a suitable adhesive. Preferably basket wires 168 are encapsulated in membrane 170.

Basket 169 may be somewhat cylindrical in its middle with tapered, conical, proximal and distal portions. Alternately, basket 169 may be slightly spherical, optionally with a flat, cylindrical middle portion. Preferably basket 169 is from about five to about forty mm in length and from about two to about thirty mm, or from about two to about twenty mm, in diameter at its widest.

The proximal end of the sheath 166 is attached to control handle or guidewire torquer 186. Control handle 186 has an opening 188 for core wire 164 so that sheath 166 can move slidably over core wire 164. For example, when sheath 166 is moved distally toward basket wires 168, filter membrane 170 collapses. Also, there may be instances where sheath 166 will be removed proximally so that other catheters or cardiovascular appliances can be introduced over core wire 164. Control handle 186, which functions as a torque device, also primarily functions to lock sheath 166 to core wire 164 during insertion.

There are a number of known, commercially available guidewire torquers that may be modified to function as control handle 186. Modification includes, but is not limited to, providing a slightly larger central lumen.

Figure 2:
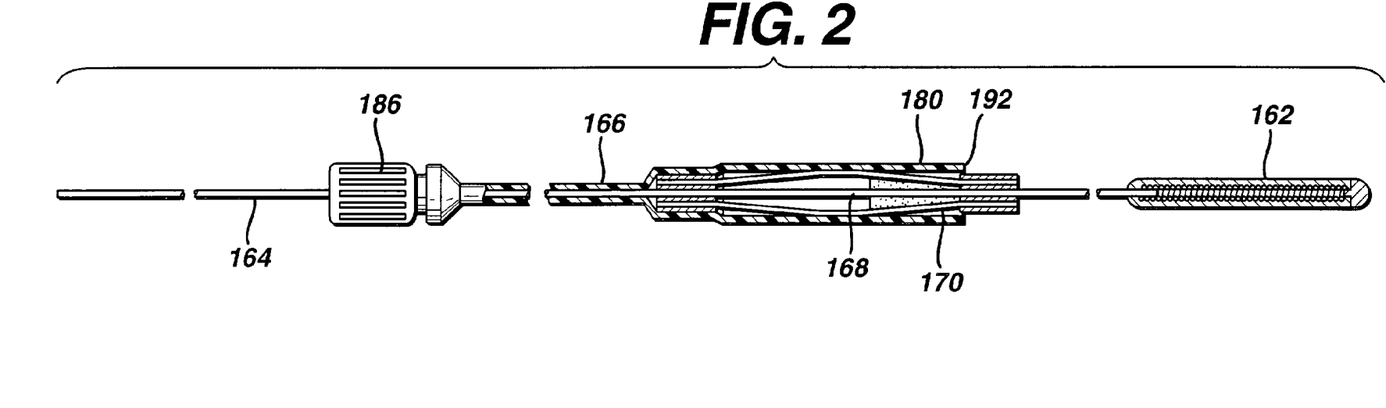
FIG. 2 illustrates a lateral, partial cross-sectional view of the exemplary embodiment of the present invention in FIG. 1 with the sheath closed.

In FIG. 2 sheath 166 and sheath member 180 are shown advanced distally so that basket wires 168 and filter member 170 are collapsed against core wire 164. The distal end 192 of sheath member 180 may optionally be slightly tapered to provide a better profile for insertion.

Figure 3:
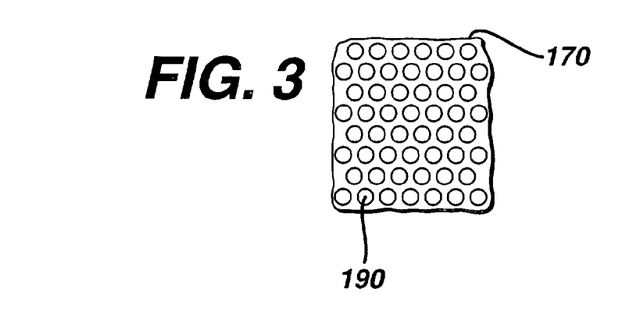
FIG. 3 illustrates a schematic representation of a portion of a filter membrane in accordance with the present invention.

In an exemplary embodiment of the present invention, as shown in FIG. 3, filter membrane 170 comprises a polymeric material such as polyurethane or silicone elastomer that has laser-drilled holes 190. Alternately, the filter membrane 170 may comprise fabric or non-fabric meshes, such as those used in known hemodialysis filters or heart-lung bypass machine filters. Suitable materials include polymers or physiologically acceptable metals or alloys.

Such holes 190, a pattern for which can be seen in FIG. 3, are preferably only on the conical portion of filter membrane 170. The holes 190 could be from about twenty to about three hundred microns in diameter. The vertical row separation of holes 190 may be from about 1.2 to 1.4 times the hole diameter and the center-to-center diameter of holes 190 may be from about 1.4 to 1.6 times the hole diameter, or in an exemplary embodiment the vertical and horizontal spacing of the holes is such that the center-to-center spacing of the holes is from about 1.2 to 2.0 times the hole diameter. Preferably the open area of the holes represents from about ten to fifty percent, more preferably from about ten to forty percent of the filter surface. Alternatively, the hole size may be variable. The mesh should have pores of a size sufficient to block and capture any micro- and macro-emboli which may flow downstream from the site where the stenosis is being treated, but large enough such that blood flow is not impeded. The mesh used in the filter device of the invention may have a pore size of from about twenty to about three hundred microns, preferably from about fifty to about one hundred fifty microns. Moreover, the size of filter membrane 170 is such as to allow a firm fit between filter membrane 170 and an artery wall (not shown). The diameter of filter membrane 170 will be directly related to the artery being treated, with typical diameters ranging from about two mm to about forty mm, most preferably from about two mm to about twenty mm.

Basket wires 168, illustrated in FIGS. 1 and 2, may comprise a suitable, physiologically acceptable metal. Stainless steel or nitinol are preferred, although titanium or other metal alloys could be used.

Figure 4:
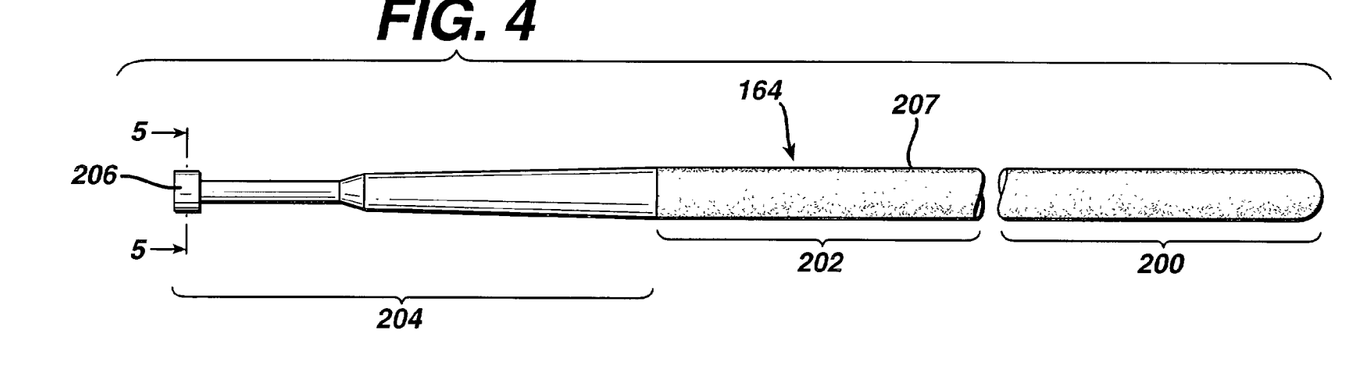
FIG. 4 illustrates a lateral view of a core wire in accordance with the present invention.
Figure 5:
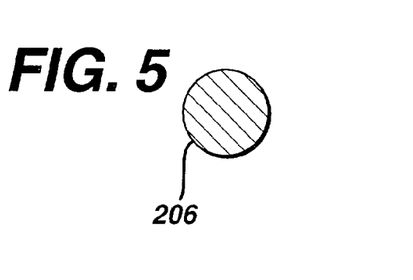
FIG. 5 illustrates a cross-sectional view across section line 5-5 of a portion of the core wire of FIG. 4.

Core wire 164 can be seen better in FIG. 4, where the proximal and middle portions 200 and 202 are substantially uniform in diameter, and then the distal portion 204 tapers to an end point 206. In fact, distal portion 204 could taper uniformly or, more preferably, non-uniformly, as shown in FIG. 4. Typically core wire 164 is from about two hundred fifty to three hundred cm in length, with an initial diameter of from about 0.009 to 0.038 inches, preferably from about 0.014 to 0.018 inches. Distal section 204 is typically from about eight to ten cm. With a diameter that tapers to from about 0.001 to 0.005inches, core wire 164 may optionally have a thin polymeric coating 207 for friction reduction. Preferably end point 206 is a solid, squat cylinder, as shown in FIGS. 4 and 5.

Floppy tip 162, as illustrated in FIG. 1, preferably comprises a radiopaque helical spring 210 that is fixedly attached, e.g., by welding, brazing, or soldering, to end point 206 and, optionally, attachment point 208. Optionally spring coil 210 may have a polymeric or lubricious coating 212.

Figure 6:
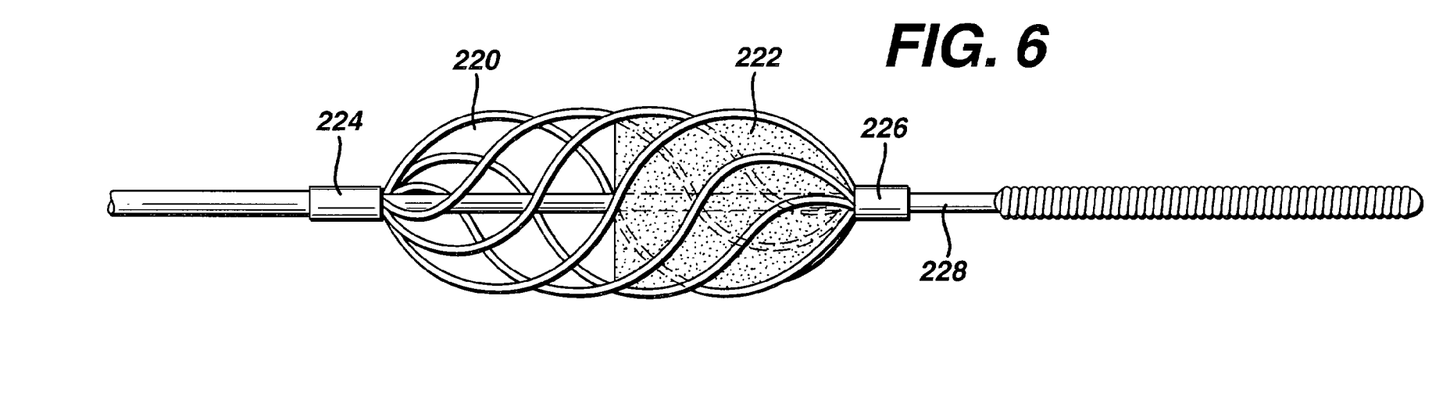
FIG. 6 illustrates a lateral, cross-sectional view of an alternate basket structure for the exemplary embodiment of FIG. 1.

FIG. 6 represents an alternate design of the vascular filter system wherein where basket wires 220 are substantially helical in shape. Filter member 222 covers or encompasses the distal portion of basket wires 220, and the proximal and distal portions of basket wires 220 are secured by proximal radiopaque marker or crimp band 224 and distal radiopaque marker or crimp band 226, respectively. Markers 224 and 226 are fixed or slidable on core wire 228 as described above. Preferably there are from four to eight basket wires 220, each with a rotation of from about forty-five degrees to three hundred sixty degrees.

Figure 7:
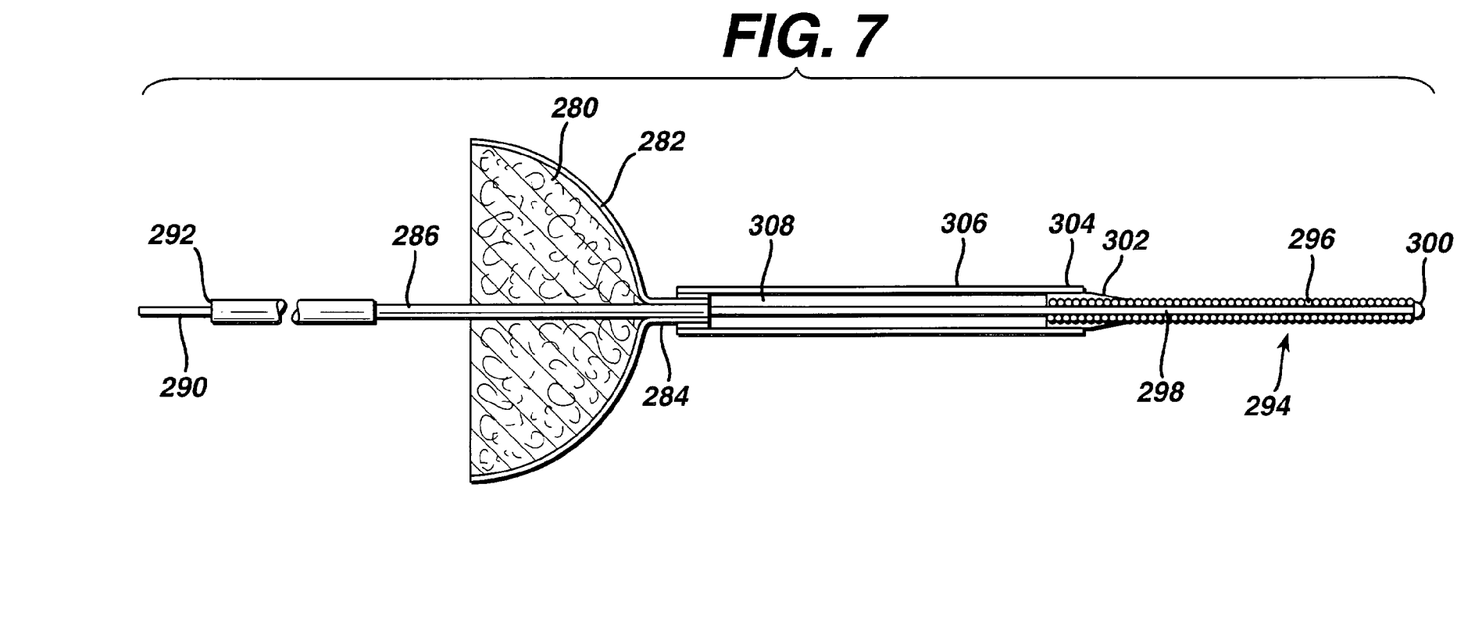
FIG. 7 illustrates a lateral, partial cross-sectional view of another exemplary embodiment of the present invention.
Figure 8:
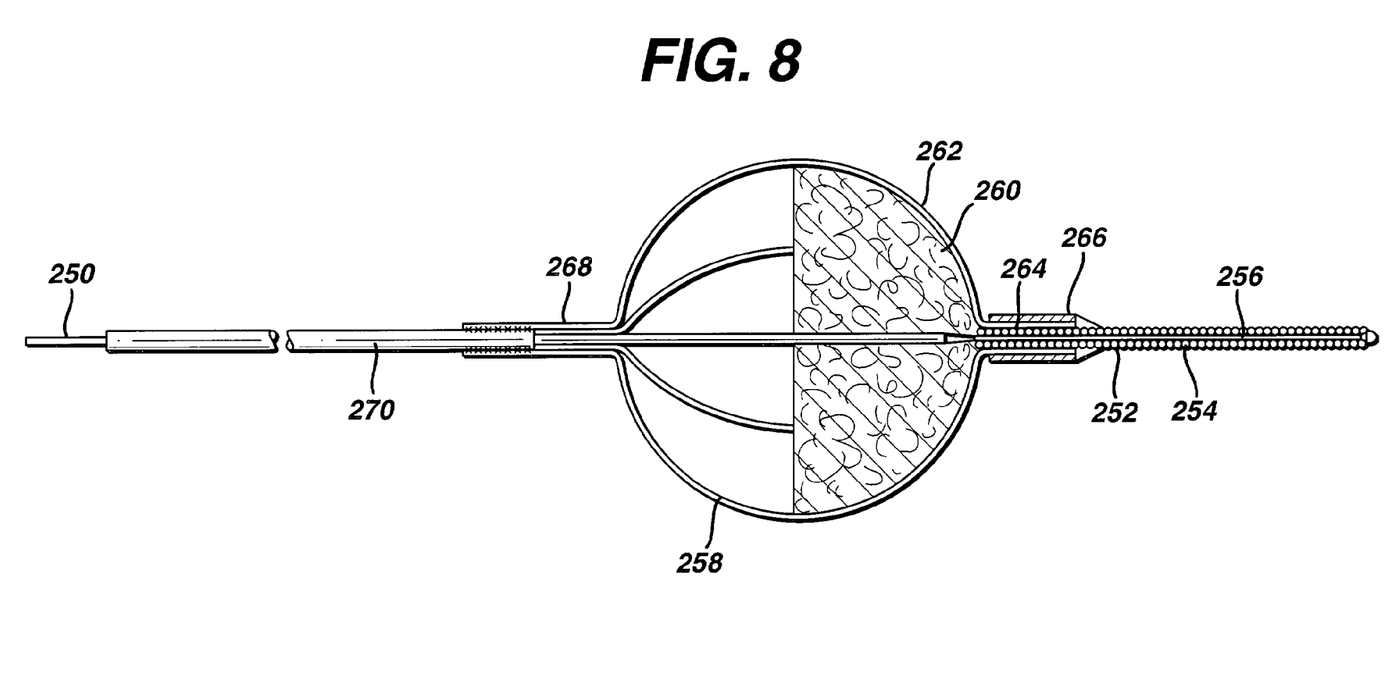
FIG. 8 illustrates a lateral, partial cross-sectional view of a further exemplary embodiment of the present invention.

Additional exemplary embodiments of the present invention can be seen in FIGS. 7 and 8. The schematic representation in FIG. 7 depicts a filter membrane 280 supported by strut wires 282. The distal ends 284 of strut wires 282 are attached to the distal portion of a tubular member 286. A movable core wire 290 extends through a lumen 292 in tubular member 286 to a distal floppy section 294, where a helical spring coil 296 surrounds the distal portion 298 of core wire 290 and is attached to end point 300. There is an attachment point 302 of weld or solder at the proximal portion of spring coil 296 where the distal portion 304 of sheath member 306 is also attached to core wire 290. The lumen 308 of sheath member 306 is large enough so that as core wire 290 is pulled proximally, or tubular member 286 is advanced distally, the distal ends 284 of strut wires 282 move into lumen 308 and collapse filter membrane 280.

Moveable core wire 250 of the structure shown in FIG. 8 comprises a floppy tip 252 where a helical spring coil 254 encompasses the distal portion 256 of core wire 250. A basket wire structure component of two or more basket wires 258 supports a filter membrane 260 on the distal portion 262 of the basket structure. Distal ends 264 of the basket wires 258 are encompassed by a radiopaque marker or crimp band 266 that is attached to core wire 250 and/or spring coil 254. The proximal ends 268 of basket wires 258 are attached to the distal portion of a sheath 270 that surrounds core wire 250. Sheath 270 moves slidably over core wire 250 so that when sheath 270 is pulled proximally into core wire 250, filter membrane 250 collapses.

Figure 9:
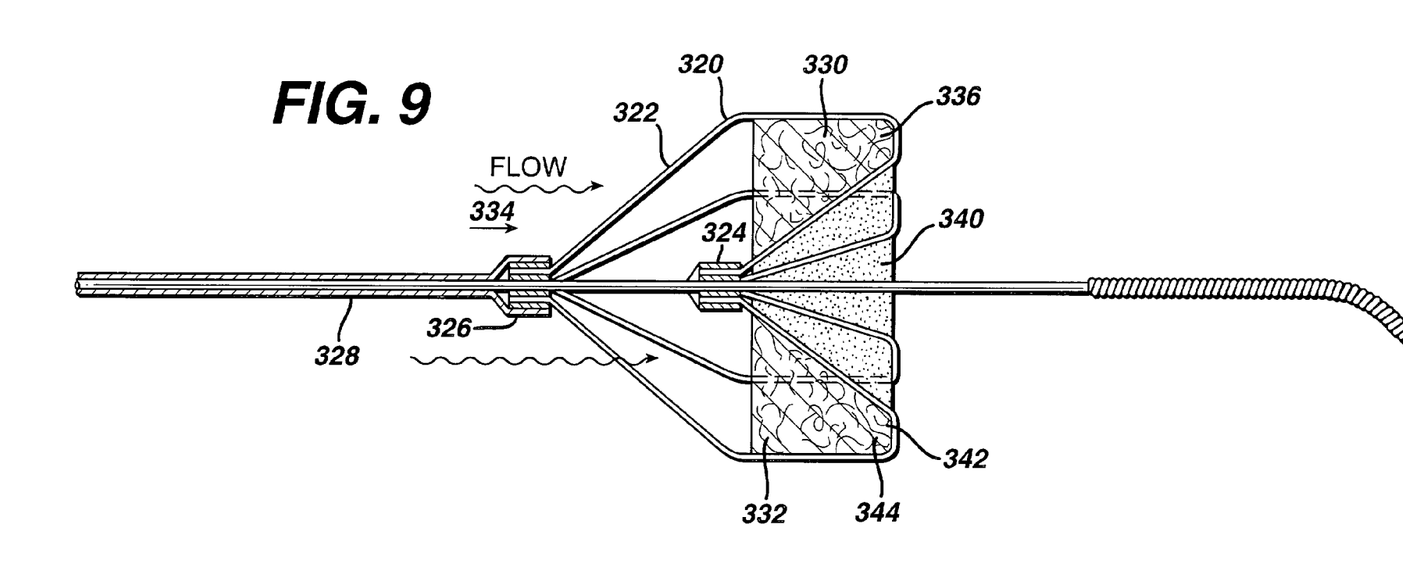
FIG. 9 illustrates a schematic, partial cross-sectional view of another exemplary embodiment of the present invention where the distal section of the filter basket is inverted.

In FIG. 9, a basket 320 comprising from four to eight strut wires 322 is secured by a distal fixed grommet 324 and a proximal slidable grommet 326. Grommet 326 is slidable over core wire 328. Filter membrane 330 is attached to or arranged upon basket 320, with the proximal section 332 of the membrane 330 being open to flow, represented by arrows 334. The distal portion 336 of membrane 330 forms a conical shape 340 that extends proximally. The filter could be deployed by, for example, a sheath or a tube fixed to the proximal slidable crimp band 326. This design is optimized for perfusion and emboli collection. For example, as more emboli is collected, it tends to collect in outer, non-filter areas, leaving the pores open for perfusion.

Membrane 330 preferably has holes only in distal section 336/340, which holes are arranged as described above. It is believed that under normal, substantially laminar flow conditions debris or emboli 342 will tend to collect in annular recesses 344.

Figure 10:
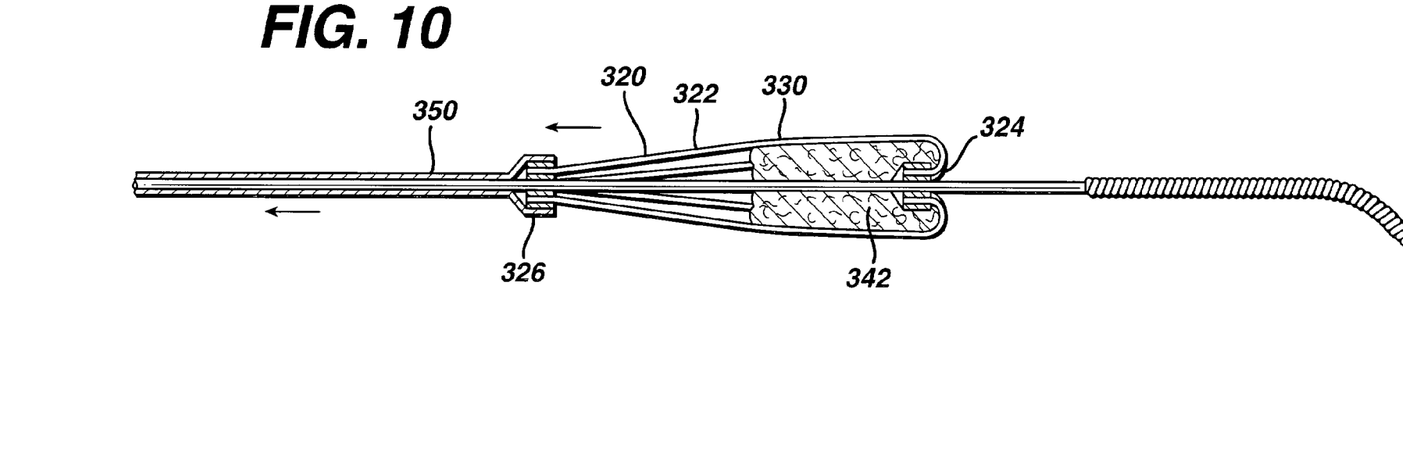
FIG. 10 illustrates a schematic, partial cross-sectional view of the exemplary embodiment shown in FIG. 9 where the filter basket is collapsed.

To close and capture emboli, as shown in FIG. 10, slidable grommet 326 is moved proximally to collapse basket 320 and membrane 330. This can be accomplished with, for example, sheath 350 or a fixed tubular member or other apparatus that is preferably slidable over the core wire.

Figure 11:
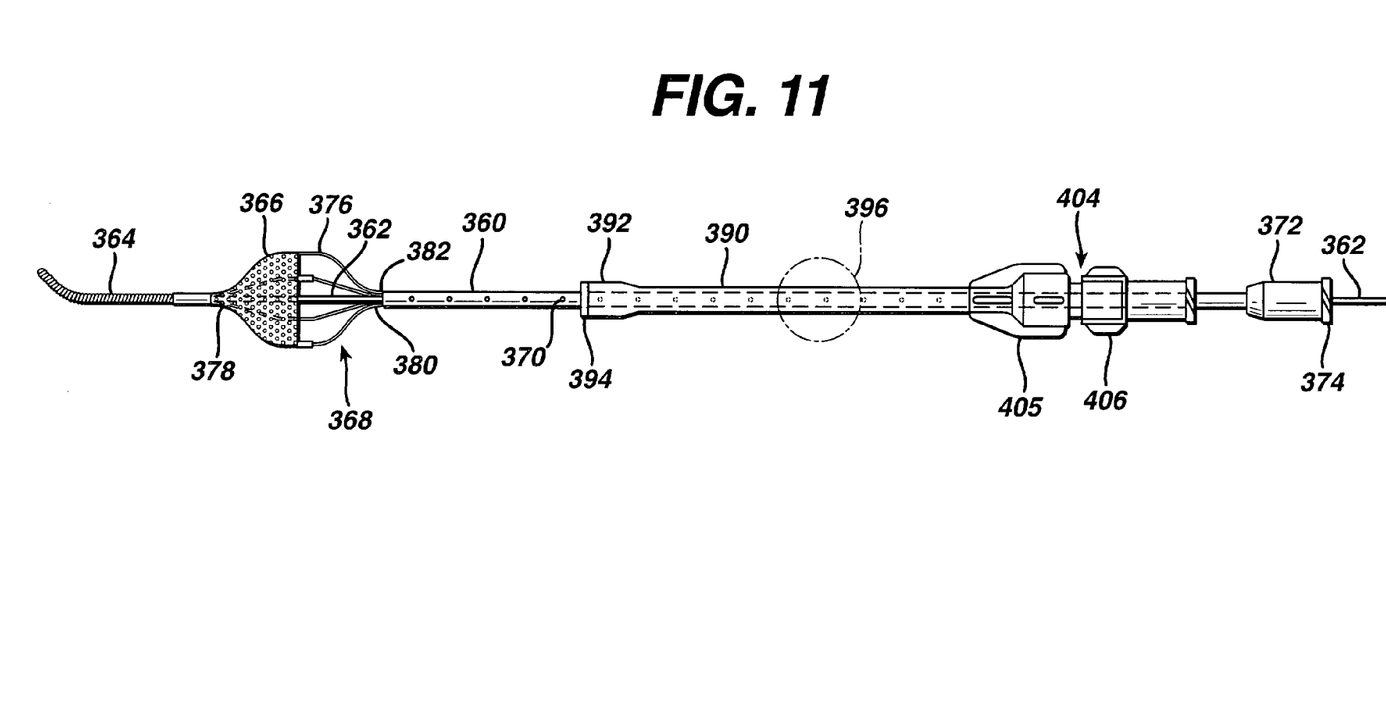
FIG. 11 illustrates a lateral, partial cross-sectional view of one exemplary embodiment of the invention with the filter membrane in an open position and guidewire having infusion holes.

In another exemplary embodiment of the present invention, shown in FIG. 11, a guidewire or rigid infusion tubing 360 extends over a core wire 362 that extends to a floppy tip 364, and a filter membrane 366 is supported by a filter basket 368. Tubing 360 extends proximally to hub 372. Core wire 362 extends through a lumen in tubing 360 and proximal to hub 372. Hub 372 has a Luer fitting 374. Filter membrane 366 supported by filter basket 368 comprises two or more filter basket wires 376, having distal ends 378 and proximal ends 380 attached to core wire 362 and operating in a manner described above in conjunction with the description of FIGS. 1-3.

The rigid infusion tubing 360 may have infusion holes 370 for delivering and distributing medication therethrough as well as through the infusion tubing end 382 to an afflicted target area of a procedure such as a peripheral thrombolysis.

A sheath 390 is connected to the sheath member 392 at its distal end and, optionally with a distal sheath marker 394, and to a locking hub 405 of a locking mechanism 404 at its proximal end. The sheath locking mechanism comprises a locking hub 405 and a latch 406 which is allowed to slide independently over the infusion tubing 360. Sheath 390 may be moved distally and proximally along the infusion tubing 360 and locked in place to prevent any further movement along the infusion tubing 360. By sliding sheath 390 distally and proximally along the infusion tubing 360, a specific number of the infusion holes 370 may be covered or opened. This covering and uncovering of infusion holes 370 thereby controls the distribution and the amount of medication along the specific area of operation, i.e., the location of the exposed infusion holes 370 relative to a thrombus 396 (or atheroma, stenosis, embolism, plaque, etc.). Infusion holes 370 may be covered and opened alternatively by distally and proximally sliding either only the infusion tubing 360 along core wire 362, distally and proximally sliding only sheath 390 along the infusion tubing 360, or manipulating both the infusion tubing 360 along the core wire 362 and the sheath 390 along the infusion tubing 360 simultaneously.

Sheath 390, sheath member 392 and locking hub 405 may be either separate pieces bonded together or a continuous, integral structure. Latch 406 is a separate piece of tubing of the same diameter as sheath 390 slidable distally and proximally along the infusion tubing 360. However, in counterdistinction of sheath 390, latch 406 has a tight fit over the infusion tubing 360, enabling sheath 390 to be secured in a secured position when locking mechanism 404 is engaged or locked.

The wires, membrane, and other materials of this exemplary embodiment are consistent with those described above.

Figure 12:
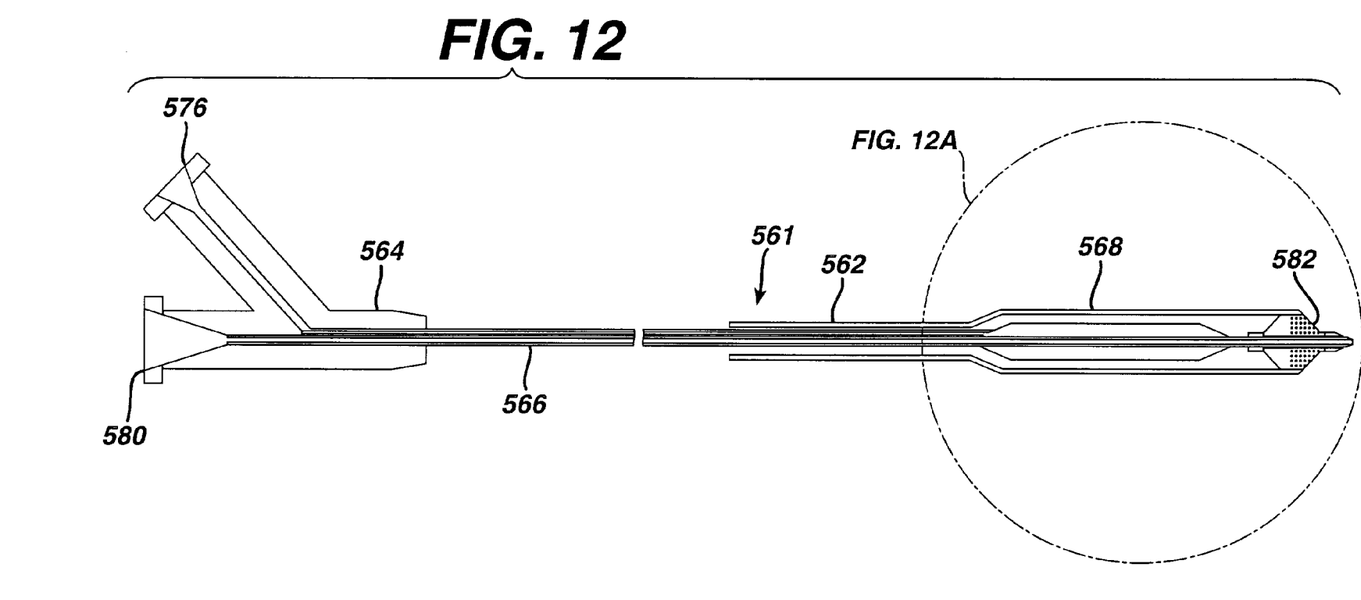
FIG. 12 illustrates a schematic, partial cross-sectional view, with an enlarged section (FIG. 12A), of an exemplary embodiment of the present invention wherein a dilatation delivery system comprises a vascular filter
Figure 12A:
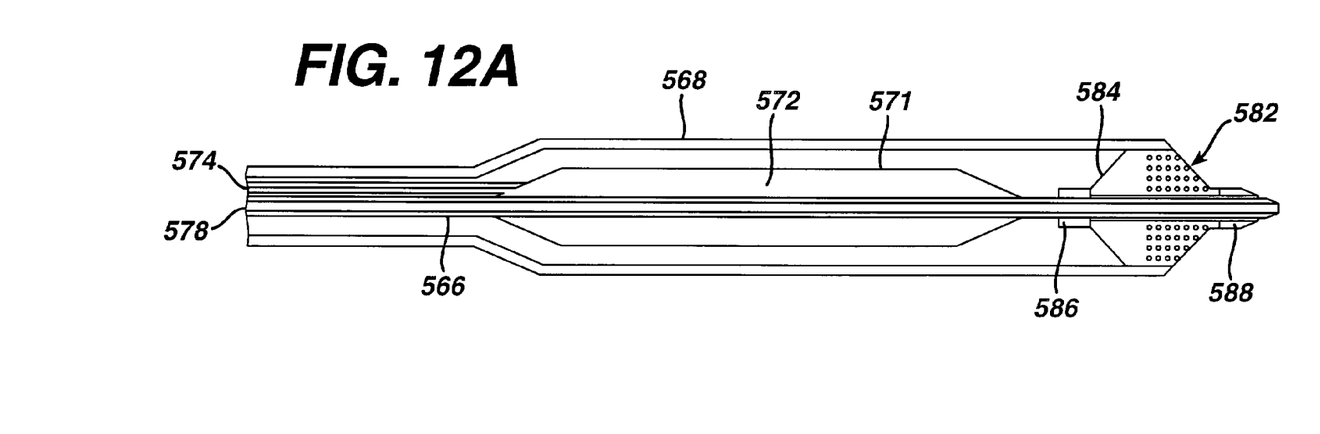

In another exemplary embodiment of the invention shown in FIG. 12 and FIG. 12A, a dilatation balloon delivery system 561 comprises a deployment sheath 562 and a hub 564. A balloon shaft 566 extends from hub 564 to the distal section 568 of deployment sheath 562, where the distal portion of balloon shaft 566 comprises an inflatable dilatation balloon 571. The interior 572 of balloon 571 is in fluid communication with inflation lumen 574 in balloon shaft 566 and an inflation port 576 in hub 564. Balloon shaft 566 also comprises a guidewire lumen 578 in fluid communication with a guidewire port 580 in hub 564 and extending through balloon 571 to a vascular filter or emboli capture device 582, as described above. The ends of a filter basket 584 are secured in a fixed grommet 586 and a slidable grommet 588.

During insertion of the dilatation balloon delivery system according to the present invention, deployment sheath 562 is advanced through a patient's vascular system to a desired location. During this stage of the procedure balloon 571 is collapsed, and vascular filter 582 is somewhat compressed. After balloon 571 is in position, deployment sheath 562 is pulled in the proximal direction, and then balloon 571 is expanded to dilate a vessel. Vascular filter 582 expands as grommet 588 slides in the proximal direction.

Once the dilatation balloon 571 is collapsed, sheath 562 may be advanced distally to collapse vascular filter 582. After vascular filter 582 is collapsed, sheath 562, collapsed balloon 571, and collapsed vascular filter 582 may be withdrawn together in the proximal direction.

Figure 13:
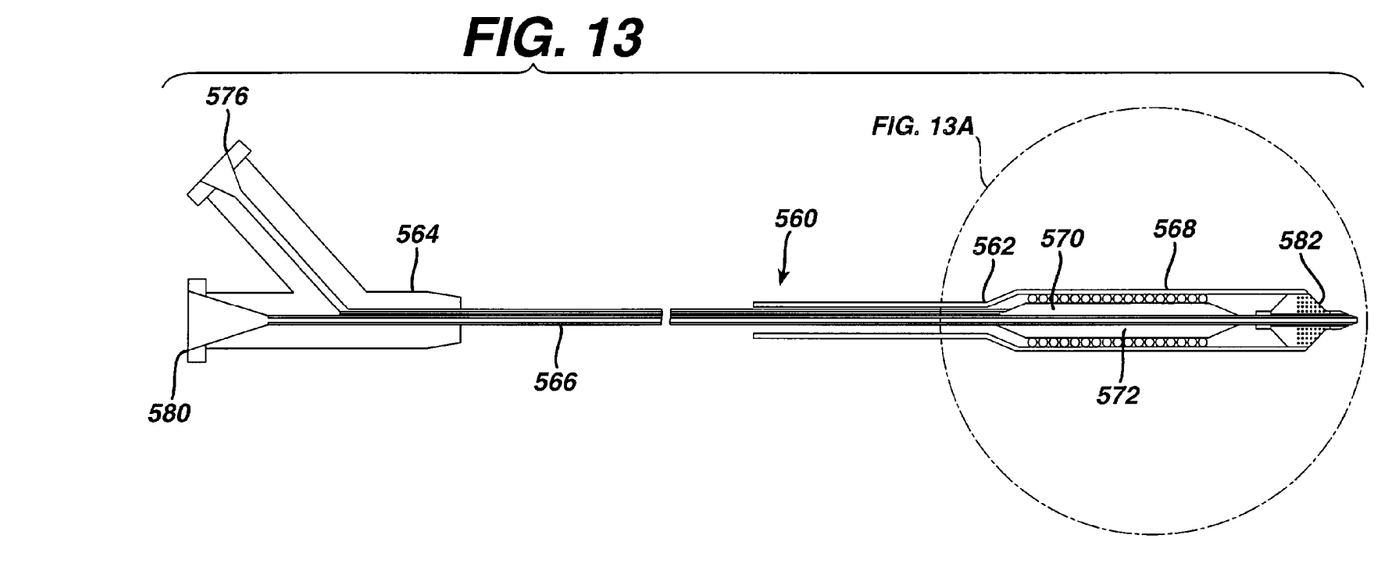
FIG. 13 illustrates a schematic, partial cross-sectional view, with an enlarged section (FIG. 13A), of an exemplary embodiment of the present invention wherein a stent delivery system comprises a vascular filter.
Figure 13A:
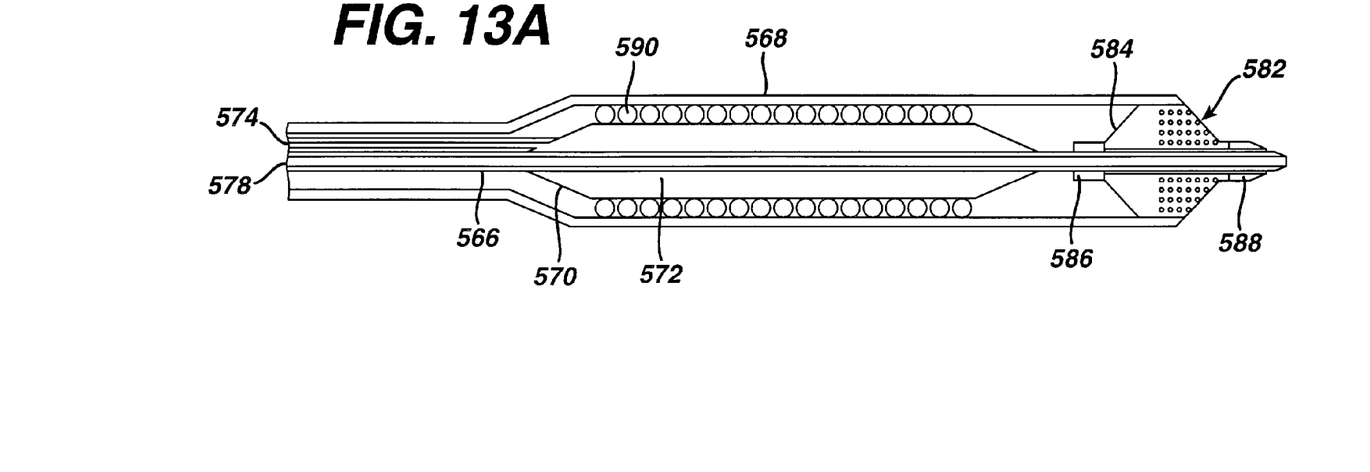

In another exemplary embodiment of the invention shown in FIG. 13 and FIG. 13A, a stent delivery system 560 comprises a deployment sheath 562 and a hub 564. A balloon shaft 566 extends from hub 564 to the distal section 568 of deployment sheath 562, where the distal portion of inflatable balloon catheter shaft 566 comprises an expandable balloon 570. The interior 572 of balloon 570 is in fluid communication with an inflation lumen 574 in balloon catheter shaft 566 and an inflation port 576 in hub 564. Balloon shaft 566 also comprises a guidewire lumen 578 in fluid communication with a guidewire port 580 in hub 564 and extending through balloon 570 to a vascular filter or emboli capture device 582, as described above. The ends of a filter basket 584 are secured in a fixed grommet 586 and a slidable grommet 588. An expandable stent 590 is positioned annularly adjacent to balloon 570.

During insertion of the stent delivery system according to the present invention, deployment sheath 562 is advanced through a patient's vascular system to a desired location. During this stage of the procedure balloon 570 is either collapsed or expanded only so far as to hold stent 586 in position, and vascular filter 582 is somewhat compressed. After stent 590 is in position, deployment sheath 562 is pulled in the proximal direction, and then balloon 570 is expanded to secure stent 590 in position. Vascular filter 582 expands as grommet 588 slides in the proximal direction.

Once stent 590 is in position, sheath 562 may be advanced distally to collapse vascular filter 582. After vascular filter 582 is collapsed, sheath 562 and vascular filter 582 can be withdrawn together in the proximal direction.

In a variation of the exemplary embodiment of the invention shown in FIG. 13 and FIG. 13A, stent 590 could be a self-expanding stent that is releasably positioned on a delivery catheter. See, for example, U.S. Pat. Nos. 5,246,445 and 5,372,600. The stent delivery catheter would comprise a lumen for release wires, etc., as well as a lumen for a guidewire lumen in connection with a vascular filter system.

Figure 14:
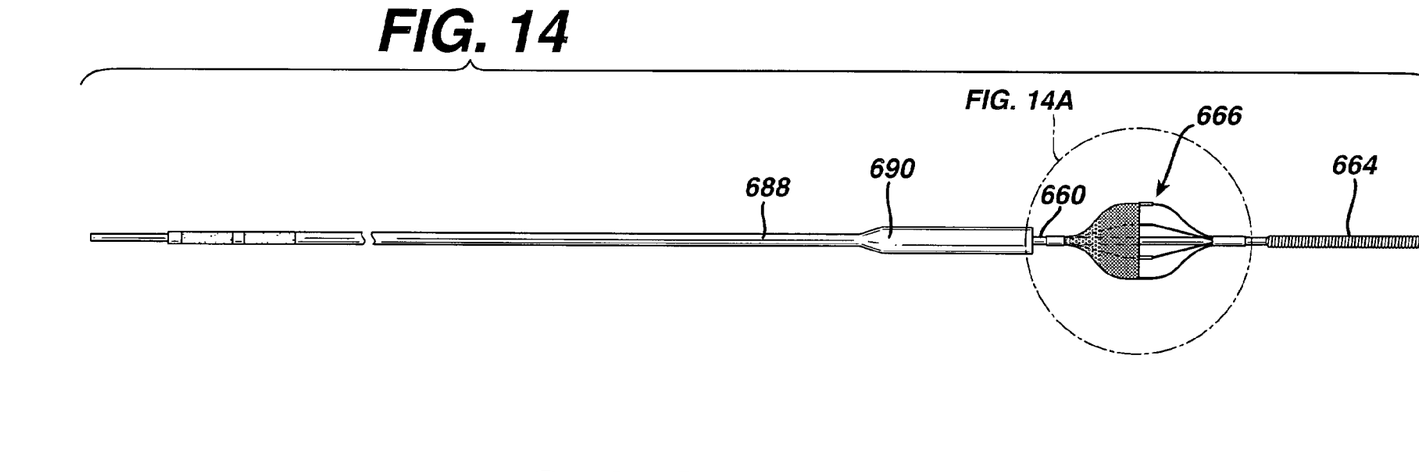
FIG. 14 illustrates a schematic, partial cross-sectional view, with an enlarged section (FIG. 14A), of an electrophysiology filter system according to the present invention.
Figure 14A:
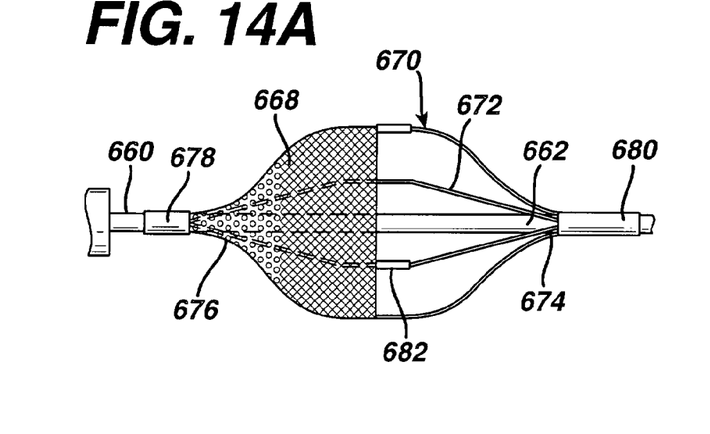

In another exemplary embodiment of the invention shown in FIG. 14 and FIG. 14A, vascular filter system comprises a guidewire 660 with a core wire 662 extending distally into floppy tip 664. Vascular filter 666 comprises a filter membrane 668 positioned in a distally facing manner on filter basket 670 comprised of six to eight struts or wires 672. The distal 674 and proximal 676 ends of basket wires 672 are held by proximal grommet 678 and distal sliding grommet 680. Optionally, filter basket 670 has radiopaque markers 682. A sheath 688 with expanded distal sheath section 690 is arranged concentrically around guidewire 660.

Consistent with the invention the vascular filter system will be inserted through a guide catheter in a patient's femoral artery and then advanced through the aorta to a position adjacent the patient's left ventricle. During electrophysiology or another ablation procedure in the left ventricle, any emboli or thrombus produced will be captured in filter membrane 668. When the procedure is complete, sheath 688 and filter basket 670 are moved relative to one another so that the distal section 690 of sheath 688 causes filter basket 670 to collapse, whereupon filter basket 670 and captured material are withdrawn with the sheath.

Figure 15:
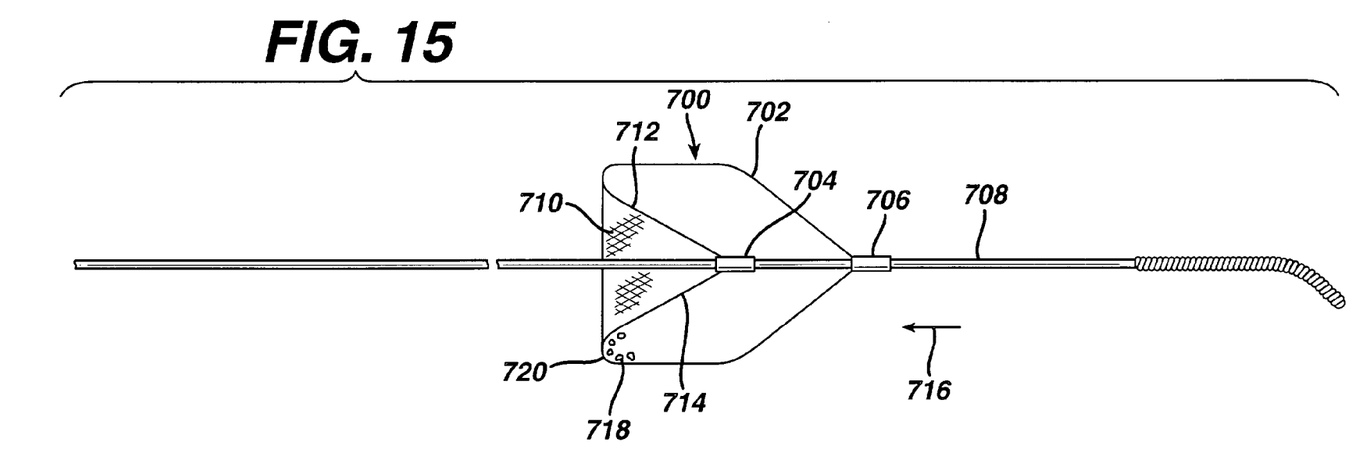
FIG. 15 illustrates a schematic, partial cross-sectional view of a filter apparatus in accordance with the present invention.

In another exemplary embodiment of the vascular filter system, the apparatus of FIG. 9 could be modified, as shown in FIG. 15. A basket 700 comprised of from four to eight strut wires 702 is secured by a proximal fixed grommet 704 and a distal slidable grommet 706. Grommet 706 is slidable over core wire 708. Filter membrane 710 is attached to or arranged upon basket 712, with the proximal section 714 of the membrane 710 being open to flow, represented by arrow 716. The proximal portion 714 of membrane 710 forms a conical shape that extends distally. The filter may be deployed by, for example, a sheath, a tube, or a wire fixed to the distal slidable crimp band 706.

Membrane 710 preferably has holes only in proximal section 714, which holes are arranged as described above. It is believed that under normal, substantially laminar flow conditions debris or emboli 718 will tend to collect in annular recesses 720.

Figure 16:
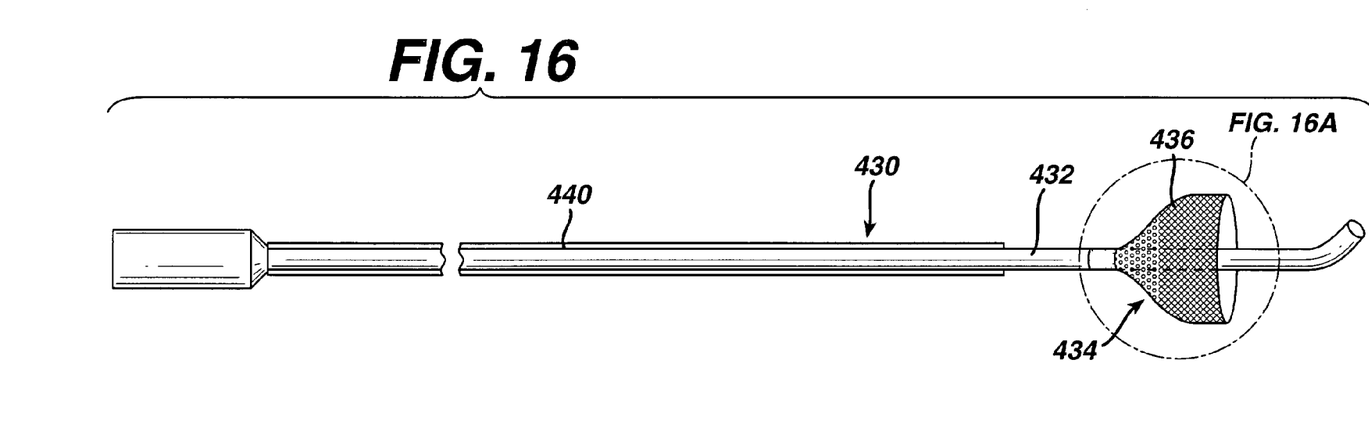
FIG. 16 illustrates a schematic, partial cross-sectional view, with an enlarged section (FIG. 16A), of a guide catheter filter system according to the present invention.
Figure 16A:
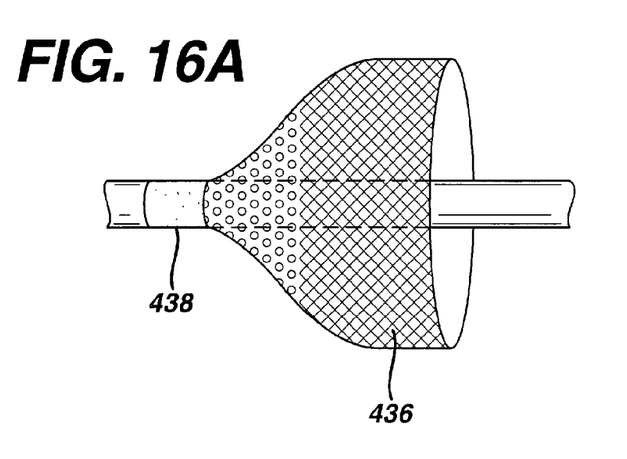

FIG. 16 and FIG. 16A depict a guide catheter 430 comprising a catheter shaft 432 having a distal end 434. A filter membrane 436 having a flexible support or structure is arranged, distally facing, on said distal end 434. The proximal portion of filter membrane 436 is secured at band 438. A sheath 440 is arranged concentrically around guide catheter shaft 432 so that when sheath 440 is advanced distally, filter membrane 436 collapses. It is contemplated that other means may be devised for collapsing filter membrane 436, such as a wire. Guide catheter 430 will preferably have a lumen 442 capable of receiving another device, such as an ablation catheter (not shown).

In accordance with the present invention, the distal portion of the guide catheter will be advanced through the femoral artery into the left ventricle.

Figure 17:
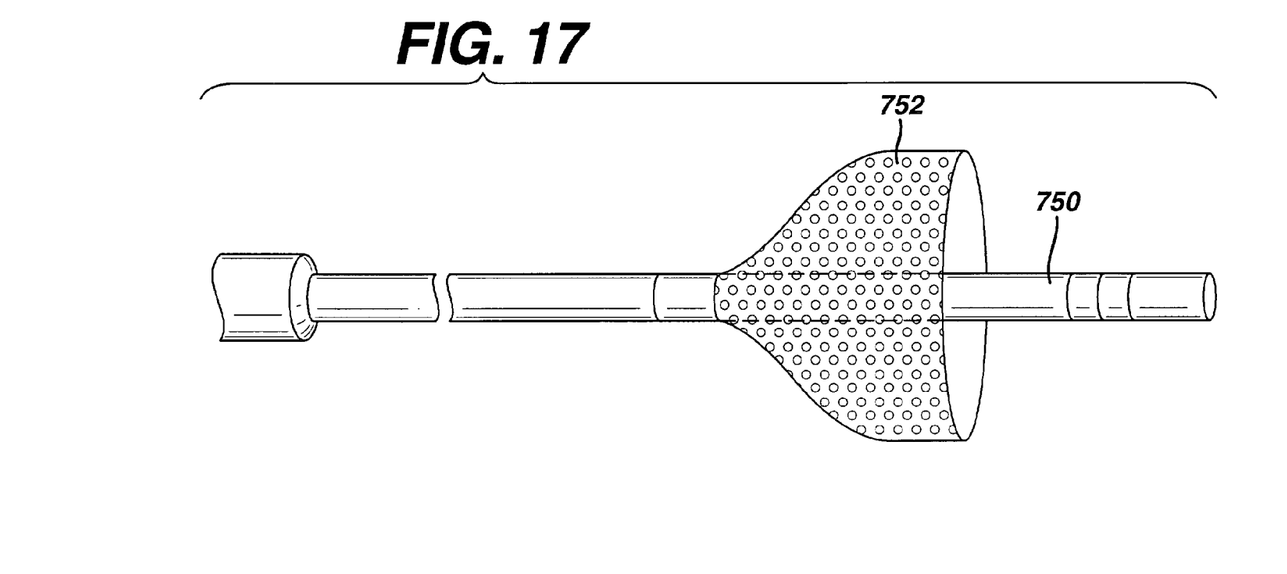
FIG. 17 illustrates a partial view of an ablation catheter in accordance with the present invention.

In another exemplary embodiment of the invention, as shown in FIG. 17, an ablation catheter 750 may have a filter membrane 752 arranged proximal to the distal end of catheter 750 by means discussed above, such as a sheath concentric to the catheter or a wire, or other means.

The preceding specific exemplary embodiments are illustrative of the practice of the invention. It is to be understood, however, that other expedients known to those skilled in the art or disclosed herein, may be employed without departing from the spirit of the invention or the scope of the appended claims.

What is claimed is:

1. A removable, percutaneously delivered vascular filter for blocking and capturing micro and macro emboli in a chamber of the heart comprising:

a catheter shaft having proximal and distal ends and a lumen configured to receive a second medical device and extending therethrough;

a distally facing, single walled, collapsible filter membrane having an open distal end, a closed proximal end, the open distal end defining a volume that is configured to receive particulate matter in a chamber of the heart as the blood flows into the open distal end, the filter membrane is fixedly secured to the catheter shaft via a single band only at its closed proximal end, such that the closed proximal end is constrained from movement along the catheter shaft and the open distal is configured to make contact with the catheter shaft when in a collapsed position, the collapsible filter membrane comprising a tapered section proximate the single band and cylindrical section for making contact with the lumen in which the membrane is positioned, the cylindrical section comprising approximately half of the length of the membrane for making contact with the lumen, the catheter shaft extending distally beyond the single walled filter membrane; and a sheath arranged concentrically around the catheter shaft, the sheath being moveable relative to the catheter shaft so that the filter membrane is deployed when the sheath is retracted and closed when the sheath is advanced, the sheath configured to trap particulate matter in the single walled filter membrane when the sheath is advanced to cover and collapse the single walled filter membrane.

* * * * *